United States Patent [19]
Berta

[11] Patent Number: 5,234,099
[45] Date of Patent: Aug. 10, 1993

[54] COATED MEDICAMENTS AND APPARATUS AND METHODS FOR MAKING SAME

[75] Inventor: Norbert I. Berta, Devon, Pa.

[73] Assignee: McNeil-PPC, Inc., Milltown, N.J.

[21] Appl. No.: 483,159

[22] Filed: Feb. 22, 1990

Related U.S. Application Data

[63] Continuation-in-part of Ser. No. 16,914, Feb. 20, 1987, Pat. No. 4,820,524, and a continuation-in-part of Ser. No. 190,551, May 5, 1988, Pat. No. 4,966,771, and Ser. No. 190,616, May 5, 1988.

[51] Int. Cl.⁵ .............................................. B65G 47/00
[52] U.S. Cl. ........................... 198/803.01; 198/803.14
[58] Field of Search ........................ 424/474, 475, 451; 198/803.01, 803.2, 465.1, 465.2, 465.3, 803.14, 803.15, 483.1, 803.13; 118/500, 30, 503

[56] References Cited

U.S. PATENT DOCUMENTS

| | | | |
|---|---|---|---|
| 2,344,000 | 3/1944 | Read | 198/803.15 X |
| 2,823,789 | 2/1958 | Henning | 118/500 X |
| 3,150,765 | 9/1964 | Ellis | 198/803.01 X |
| 3,181,689 | 5/1965 | van der Winden | 198/803.15 X |
| 3,538,997 | 11/1970 | Christine et al. | 198/803.01 |
| 3,543,908 | 12/1970 | Holland | 198/803.13 X |
| 3,552,536 | 1/1971 | Emary | 198/465.2 X |
| 3,838,791 | 10/1974 | Raitt | 198/803.15 X |
| 3,884,143 | 5/1975 | Ackley | 198/803.01 X |
| 4,189,996 | 2/1980 | Ackley, Sr. et al. | 198/803.01 X |
| 4,522,149 | 6/1985 | Garbis et al. | 118/500 X |
| 4,735,032 | 4/1988 | Focke | 198/803.15 X |
| 4,965,089 | 10/1990 | Sauter et al. | 118/30 X |
| 5,054,258 | 10/1991 | Tait et al. | 198/803.14 X |

FOREIGN PATENT DOCUMENTS

| | | | |
|---|---|---|---|
| 0445365 | 6/1927 | Fed. Rep. of Germany | 198/803.1 |
| 0159821 | 7/1920 | United Kingdom | 198/803.14 |

Primary Examiner—Robert P. Olszewski
Assistant Examiner—James R. Bidwell
Attorney, Agent, or Firm—Joseph F. Shirtz

[57] ABSTRACT

A carrier apparatus for a plurality of a product has a plurality of collets for maintaining the product in a fixed orientation wherein two specimens of the product are retained within one collet. The collets include a circumferential depression at one end and a resilient member which serve to retain the collets in the carrier apparatus.

10 Claims, 7 Drawing Sheets

COATED MEDICAMENTS AND APPARATUS AND METHODS FOR MAKING SAME

This is a continuation-in-part of U.S. patent application Ser. No. 016,914, filed Feb. 20, 1987, entitled "Gelatin Coated Caplets and Process for Making Same" which issued on Apr. 11, 1989 as U.S. Pat. No. 4,820,524; and is a continuation-in-part of Ser. No. 190,551, filed May 5, 1988 U.S. Pat. No. 4,966,771; and Ser. No. 190,616, filed May 5, 1988.

BACKGROUND OF THE INVENTION

The present invention relates to improved coated medicaments and apparatus and methods for making such improved products.

The desirability of manufacturing medicaments having a gelatinous or other coating is pointed out in U.S. Pat. No. 4,820,524 which is incorporated in its entirety herein by reference. Although the invention disclosed therein fulfilled, to a certain extent, the need for a coated medicament which is at least as a tamper resistant as a caplet, yet still provides the ease of swallowability of a capsule, the need for further refinements in this regard remains unmet.

The concept of coated pills and tablets is well known in the art. There are numerous reasons for employing such coatings. Most frequently, the coating will either protect the linings of the digestive tract from direct contact with the compressed tablet or provide a time release function by slowing the dissolution rate. In many instances, coatings also protect the tablets from physical damage or deterioration during shipment and handling.

Numerous medicaments have traditionally been provided by filling hard gelatin capsules with active ingredients. The unexpected increase in the occurrence of product tampering incidents involving hard gelatin capsules created an urgent need for new tamper resistant packaging. In creating such packaging, an important factor was the retention of the physical characteristics of a gelatin capsule. There exists evidence that gelatin coated medicaments are easier for many patients to swallow. Additionally, there is a perception that medicaments provided in hard gelatin capsules are more effective. This latter effect is similar to the placebo effect, patients maintaining that a capsule form medicament is more effective, even if the non-capsule form prescribed is of equal pharmacological effectiveness.

In response to this need, it has been found that an oblong-shaped caplet, or other solid form of medicament may be coated with gelatin to provide both the easier swallowability and the outward appearance of a hard gelatin capsule. Accordingly, U.S. Pat. No. 4,820,524 provides a coated medicament which is at least as tamper-resistant as a caplet, while providing the easy of swallowability of a gelatin capsule. The capsule-like medicaments provided have smooth, relatively thick, shiny, multi-colored gelatinous coatings thereon. The medicaments disclosed are pleasing to the eye and are intended to be perceived by patients to be easier to swallow and more effective than caplets having other coatings, while providing greater tamper resistance than conventional capsules.

Other types of coatings in addition to gelatin are known to those of ordinary skill. For example, U.S. Pat. No. 4,585,764—Bailey discloses combining aspirin with 3.3'-hiobis, while U.S. Pat. No. 4,590,183—Bailey provides combining aspirin with sodium thiosulfate. Both Bailey patents are directed to the cytoprotection of gastric mucosa using the coatings described. U.S. Pat. No. 4,713,248—Kjern, et al, discloses a coating for a medicament comprising a polymer film which provides a controlled release coating. The preferred coating is a substantially water insoluble but water diffusible polymer. An improved tablet or caplet comprised citric, alginic or glutamic acid is disclosed in U.S. Pat. No. 4,716,042—Blank, et al. Undoubtedly, those of ordinary skill are aware that these and other coatings may be modified, combined or used in conjunction with one another. Moreover, certain of these may be useful in combination with gelatin to form a coated product in accordance with the present invention.

Although the coated caplets disclosed in U.S. Pat. No. 4,820,524 described immediately above provide a novel and superior product which has met with outstanding commercial success, that success has created new challenges and a need for further refinements and improvements. For example, at present, coated caplet products having different portions of the coating overlapped to form a seam, thereby creating a simulated capsule-like medicament are most preferably provided. However, the overwhelming acceptance of gelatin coated caplets has created a need for variations to the original product. In other instances, it may be preferable that the coatings do not overlap, but instead leave a "line" of underlying uncoated material. These embodiments may be preferable for brand identification or for other purposes. Also, it has now been found that the simulation of a capsule-like appearance may no longer be necessary to overcome any consumer acceptance problems which may have initially existed.

Although methods of producing pills having smooth continuous gelatin coatings are generally known, products produced by such methods are necessarily of limited utility. For example, U.S. Pat. No. 599,865—Richards discloses fully coated pills produced by a method which eliminates holes or discontinuities caused by the point of contact with pill handling apparatus used at that time. Richards, however, provides no teaching regarding the creation of a product having two or more colors or the control of the extent to which the pill is coated, e.g. one-half, one third, etc. Thus, there exists a need for gelatin coated products which are dipped in gelatin and do not have a seam created by the overlap of the two coatings even if only one color is used.

Despite the teachings of the patents referenced above and U.S. Pat. 4,820,524 which discloses an overlapped capsule-like gelatin coated product, a need remains for enhanced gelatin coated products in a wider variety of available configurations. Further, it is desirable that such coated medicaments lend themselves to efficient manufacturing processes. Although U.S. Pat. No. 4,820,524 provides an inexpensive medicament coating method capable of producing a multi-colored capsule-like coating which is perceived by the consuming public to be more effective, this and previous inventions are at best interim solutions. Previous methods and apparatus were directed to modifying existing hard gelatin capsule machinery for coating solid medicaments. This was a practical and valuable solution, allowing these novel products to be produced with a minimum lead time. The outstanding success of the product produced, however, has created an urgent need for methods and apparatus which can produce a multi-colored capsule-like coating faster, more efficiently, at higher volumes and at higher levels of coating quality and consistency than previously possible. It is further desirable to be able to introduce a variety of coating combinations beyond the "half a first color, half a second color" format generally in use, and to be able to produce these and other gelatin coated products efficiently. Finally, it is desirable to use more than one coating-of a substance or substances. Such a product may have multiple coatings which provide a smoother finish. Moreover, the products to which coatings are applied may or may not have a subcoat.

SUMMARY OF THE INVENTION

Accordingly, it has now been found that improved coated medicaments may be provided using apparatus and methods as provided herein.

In accordance with the present invention, a coated medicament to which a single or multiple first- coating and single or multiple second coating are applied is provided. In certain embodiments the medicament will have a sub-coating applied. Preferably the coating may be a polymer, sugar based, dyed cellulose, or most preferably gelatin. In a most preferred embodiment, the medicament is an oblong shaped caplet. The coatings may be applied to cover unequal portions of the caplet and may or may not overlap to form a seam.

Preferred apparatus for producing coated products are also disclosed. The apparatus of the present invention preferably comprises a hopper for retaining a plurality of products to be coated. The hopper is preferably constructed to form what is essentially a fluidized bed of product by being provided with a large volume of low pressure air. The air de-dusts the cores and also enhances feeding orientation. As a result, the formations of bubbles, lumps or other surface irregularities is minimized. The product is fed into a plurality of retainers as the retainers are advanced beneath the hopper and feeder mechanism.

Most preferably, the retainers used are double collets disposed within a carrier plate. The double collets of the present invention are most preferably substantially cylindrical and utilize one or more resilient portions to retain at least two specimens of the product in axial alignment. The collets are preferably held in place within the carrier plates using an integral shoulder at a first end and by a circumferential elastomeric member, such as an O-ring, at a second end. Alternatively, elastomeric members may be provided at each end.

The carrier plates preferably have slots or holes which permit them to be manipulated throughout the apparatus which carries out the coating process. The plates can thus be moved in a linear indexed increment, permitting the timing of the various steps of the process to be coordinated and thereby carried out more or less continuously.

In a most preferred embodiment, the feeder apparatus comprises a plurality of feeder tubes which contain a number of axially aligned product. The product is then fed, row-by-row, one from each feeder tube, into the collets within the carrier plates. The feeding is accomplished by connecting stop bars and control bars with a parallel linkage. The feeder apparatus also preferably comprises a row of pins which insert the product into the collets to a predetermined depth.

After the carrier plates are filled, row by row, with two axially disposed specimens of product, the actual coating process begins. In order to reduce bubble formation, the product is preferably preheated to the temperature of the coating. Since in a preferred embodiment a portion of each product extends beyond the edge of the collet which is retaining it, a preferred dipping apparatus comprises a dip tank and means for lowering and raising at least one of the plates into the tank, so as to coat the exposed end with the coating material contained in the dip tank.

Since in a preferred embodiment two coatings are used, after one side is lowered into the first coating material and raised, the plate is indexed and rotated one and one half times. The rotation thereby places the other side of the plate, and the uncoated, exposed product disposed therein in proximity of a second dip tank and means for raising and lowering the plate. The product is again coated by lowering the plate into a coating material contained in a dip tank, removed, and rotated one and one half times, returning the plate to its initial position. Also, a third dipping tank may be included to preferably provide a pre-coat or subcoat to the product. Further dipping tanks may be added in certain embodiments to permit further multiple coatings.

In a preferred embodiment of the dipping tank an inner and outer reservoir and a pump means are provided to keep the coating in constant circulation. Most preferably, the pump is deactivated by, for example, reducing the speed or directing the output just prior to lowering the product into the coating, thereby assuring a uniform, level surface into which the exposed ends of the product are immersed. The tanks may also preferably comprise a heater to control the temperature of the coating.

After each plate has passed through the dipping phase of the process, they are next transported to a second portion of the cycle and urged into a linear track. As before, by urging the plates against each other, the need for conveyors and the like is substantially eliminated. In this portion of the cycle, plate washing apparatus may be provided in some embodiments.

The carrier plates are next transferred to a dryer, which cures the coatings. In a preferred embodiment, a novel "spiral" dryer disposed above the dipping apparatus moves the plates through an environment of conditioned air. Alternatively, plates can be transferred into radially disposed retainers within a rotating drum-type dryer. In order to conserve energy, preferred embodiments of the dryer recirculate and reuse the heated air, rather than directly exhausting it. After the coatings have cured, the plates are removed from the dryer exit incrementally along the apparatus.

The plates move next beneath an ejector apparatus. In a most preferred embodiment, the ejector first urges a row of the products disposed within a collet against the fully coated product beneath it until it is flush with the plate. This may be accomplished in two or more stages, as the plate is incrementally advanced. As the upper product is forced axially through the collet the finished product falls free and is collected in a hopper for further processing. The remaining, half coated row of product is then preferably moved beneath a row of pins which urge them axially further through the collets into substantially the same position as the product which was ejected. Thus, the uncoated end of the product previously disposed within the plate is now exposed and the collet is open at one end, ready to receive a fresh, uncoated row of product.

Methods of coating medicaments are also disclosed. Most preferably, an uncoated Product is dipped in two or more different coating substances in one or more coats to produce products in accordance with the present invention.

DETAILED DESCRIPTION OF THE PREFERRED EMBODIMENTS

Figure 1A:
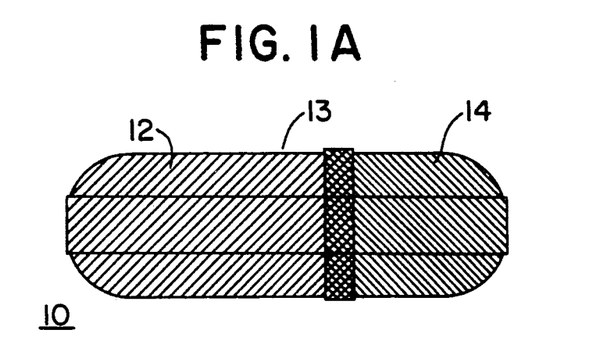
FIGS. 1A-1C depict representative products which are made in accordance with the present invention.
Figure 1B:
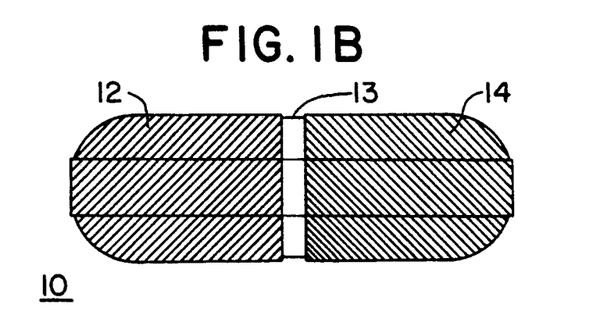
Figure 1C:
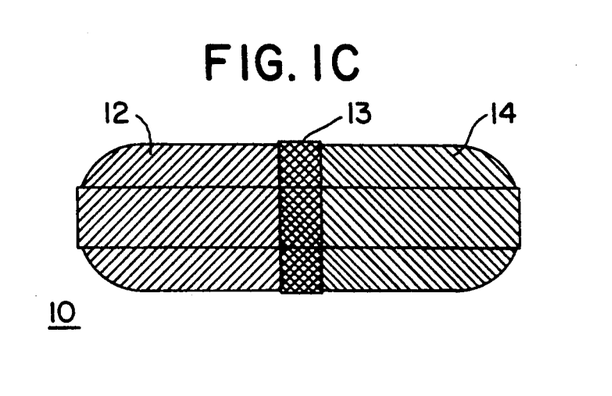

Referring to FIGS. 1A-1C, there are illustrated typical products made in accordance with the present invention. An oblong-shaped solid, gelatin coated caplet 10 is shown having a first coating 12, a second coating 14 and a seam area 13. In certain embodiments, as shown in FIG. 1A, the two coatings may cover unequal portions of the product surface area. Additionally, the two coatings 12,14 need not necessarily meet, as illustrated in FIG. 1B. The seam area 13 in this embodiment is an area devoid of either coating 12,14 which preferably is the color of the underlying caplet. On the other hand, as shown by FIG. 1C, the present invention also encompasses embodiments wherein the two coatings 12,14 overlap to an extent and form a seam 13 which simulates a capsule. It will be understood by those of ordinary skill that the embodiments of FIGS. 1B and 1C may be produced to have unequally coated portions as shown in FIG. 1A. The two coating materials 12,14 may be comprised of the same material or different materials and may be applied in one or two or more coats.

In certain embodiments, the caplets or other coated products of the present invention will comprise a subcoating. Most preferably, the subcoating will also be applied to the entire surface of the uncoated product. At a time prior to the implementation of the present invention, the product may be preferably compressed and pan coated with a subcoat. Such subcoatings are well known in the art, for example the subcoat "OPADRY TM" manufactured by Colorcon, a division of Berwind Pharmaceutical Services, Inc., 415 Moyer Blvd., West Point, Pa. 19486 has been found to provide good results when used in conjunction with the present invention. This particular subcoat may also be tinted using the product "OPATINT TM" by the same manufacturer. Alternatively, the subcoat may be omitted, or performed as a result of the apparatus and methods of the present invention, the choice dictated by the preference of the manufacturer and the economics of the product.

The coatings which are applied to the products of the present invention may be any of a number of different substances. As pointed out above and as is well known to those of ordinary skill, the choice of a particular coating is dependent upon the product being coated and the methods and apparatus being used to apply the coating. In a most Preferred embodiment of the present invention, an oblong-shaped caplet is coated at each end with a different color coating. Accordingly, it has been found that a gelatin or gelatinous substance provides good results. Alternatively, coatings comprised of polymers or polymeric compounds could be used Coatings comprised of sugar, dyed cellulose or collagens are also useful alternatives to make the products disclosed herein.

In general terms, the apparatus of the present invention includes means for rotating and otherwise transporting the carrier plates from point to point, as well as altering their relative spatial orientation and distribute the gelatin evenly on the surface. The plates are rotated, allowing each side to be respectively lowered into a gelatin tank. Transport means are then used to carry the plates to an oven which is used to dry both sides of the plate and the exposed product simultaneously. This reduces energy consumption and decreases cycle time, allowing for a high volume to be produced. However, even with the improved technology used, the drying time for the gelatin coating is still somewhat slow, requiring about thirty-five minutes to be sufficiently cured. Thus, the preferred apparatus comprises either a section where the coated product remains while drying, or most preferably comprises a conveyor section through which the coated product moves while drying. This latter solution is most preferable since it permits the machine to be run at a continuous, single speed. The apparatus is most preferably run at a speed of about 48-60 advances per minute, which translates to about 0.4-0.5 inches/second.

Figure 2:
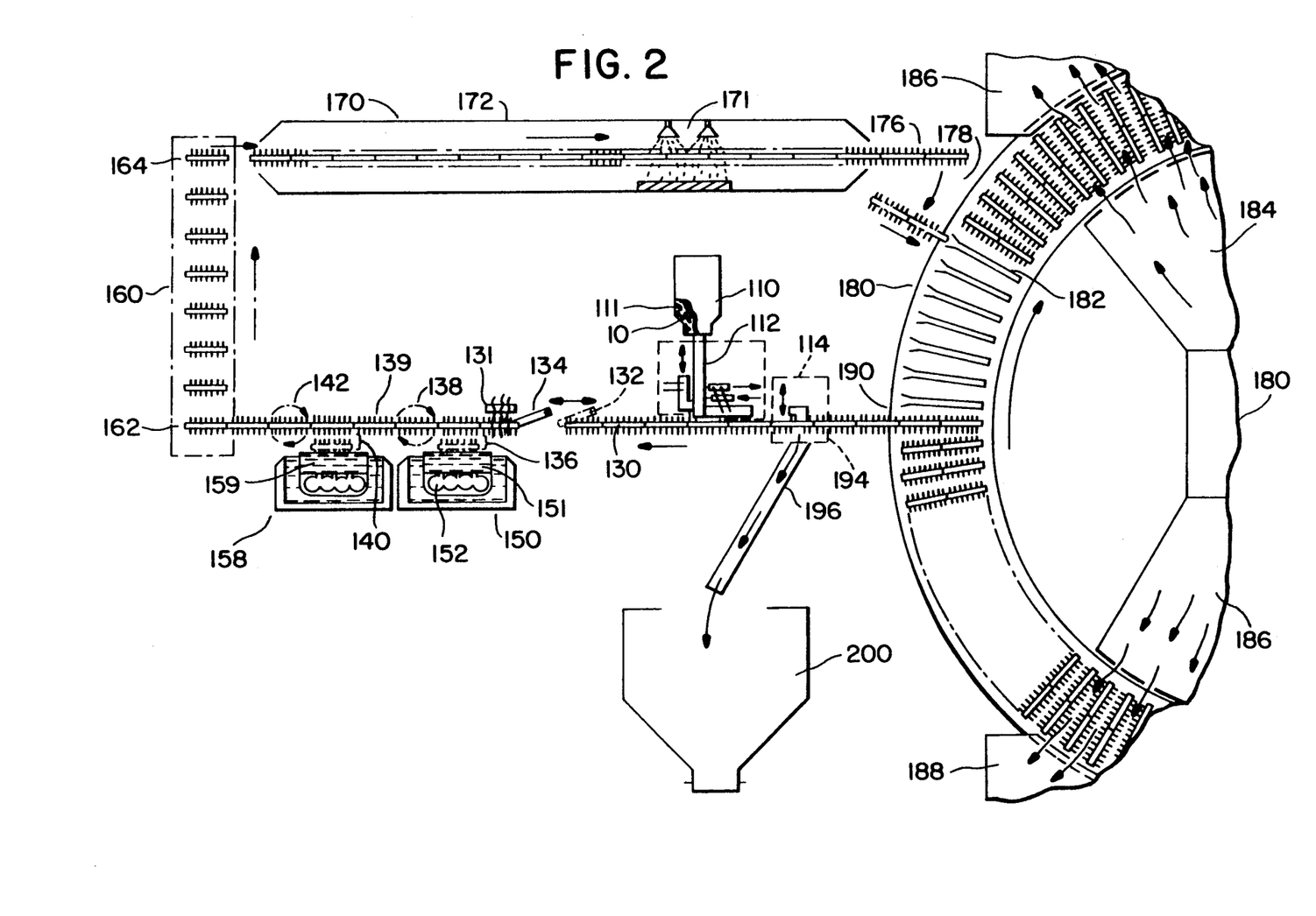
FIG. 2 is a partially schematic, partially diagrammatic illustration of a preferred embodiment of the apparatus of the present invention.

Referring now to FIG. 2, a partially schematic representation of a preferred embodiment of the apparatus of the present invention is shown. A hopper 110 is provided which contains a plurality of the product to be coated. In a most preferred embodiment, the hopper 110 will contain a plurality of caplets 10 similar to those illustrated in FIGS. 1A-1C before they were coated. The hopper 110 orients the products so that the feeder apparatus 114 is provided with the correct number of products in the correct orientation. The hopper system of the present invention most preferably makes use of a fluidized bed feeder to orient and de-dust the product to be coated. The use of this apparatus in the present invention provides unexpected and improved results. By creating a vacuum in the feeder tubes 112 and supplying the feeder bin 111 with a large volume of low pressure air, a fluidized bed is essentially created. The unexpected benefit of this apparatus, in addition to the improved material handling characteristics, is that any powder or other loose matter clinging to the uncoated product 10 is dislodged and carried away, thus providing a superior surface to which coatings more readily and uniformly adhere. Further details of the feeder apparatus 114 are discussed below with reference to FIG. 12.

The feeder apparatus 114 acts in coordination with a plate 130 which moves relative to it. As each plate 130 moves beneath the feeder apparatus 114, a row of product is correctly positioned and inserted into spaces within the plate 130, the details of which are explained below. The advancement of each plate 130 also advances the plates which have been filled. Thus, by pushing the leading edge of a first plate against the trailing edge of the plate in front of it, the need for conveyors or other means for moving the plates is eliminated. The incremental length of each advance is equal to the pitch between rows of product. However, as shown at 132,134 in a most preferred embodiment, the rate of advancement may be increased after a plate has been filled. As illustrated, after three plates are full, one plate is advanced at a greater pitch length as shown at 132,134. By increasing the incremental length of the advancement of the plates, timing advantages are obtained which increase the overall efficiency of the production cycle. It should be noted that after the increment has been increased, the plates are again in close-spaced relation so as to urge against one another. As before, this eliminates the need for further sources of motive force to move the plates through the apparatus.

After the plates are transferred to the increased indexing portion of the cycle, the actual coating process begins. Prior to dipping the plate 130 containing product is preferably preheated by means such as a radiant heater of forced air stream 131 to the temperature of the coating to substantially avoid bubble formation. It has been observed during the development of the present invention that bubble density and size are greater on the second coated end than on the first coated end. Subsequent experiments proved that the reduction in bubbling was due to the raising of the temperature and reduction of the moisture content of the product immediately after the first dip. Therefore, it has been shown that a most desirable improvement in the smoothness and "shininess" of the coating could be achieved merely by preheating the product prior to the dipping operation.

As shown at 136, a first dipping means for lowering and raising a plate are provided. Positioned beneath the first dipping means 130 is a first coating tank 150. By lowering the exposed ends of the product 10 which have been inserted into a Plate 130 into a first coating material 151, a predetermined portion of the product is coated.

The plate 130 is then raised from the first dipping tank 150, and indexed to a first rotating means 138 for rotating a plate 130 about its longitudinal axis. Most preferably the rotation is in the direction shown and is for one and one-half revolutions, i.e., 540°. This amount of rotation results in the plate 130 being inverted relative to its position prior to rotating and, additionally, provides a sufficient time and passage through the air to evenly distribute and initially "set" the first coating 151 which is typically comprised of the coatings 12,14 visible in FIGS. 1A-1C or may be comprised of subcoating or other substances. One of ordinary skill will understand that for the latter described "set" to occur, the composition of the coating and the speed of the rotation must be chosen relative to the curing time for a given coating composition. In alternate embodiments, two and one-half, or even greater numbers of rotations may be necessary.

After the first rotation at 138, each plate 130 is advanced to a dwell location 139 and then to a second dipping means 140, which is most preferably identical to the first dipping means 136. The plate 130 is again lowered into and raised out of the second dipping tank 158, which is filled with a second coating material 159. Although the first coating material 151 and the second coating material 159 are most preferably provided in different colors, they may be the same color. Moreover, the first and second coating materials may be comprised of different compositions, although preferably they are the same coating composition and most preferably comprise a gelatin or gelatinous substance. The depth to which the exposed ends of the product may be adjusted to provide the various coating treatments described above with reference to FIG. 1A-1C. The depth the product 10 is immersed in each tank 150,158 is adjustable and is not necessarily the same.

After the plate 130 is removed from the second dipping tank 158, it is then advanced and rotated a second time, as shown at 142. The second rotation is also at least one and one-half revolutions, although variations to this amount of rotation may be necessary in certain embodiments. Once the second rotation is complete, the plate 130 has now been returned to its initial orientation. At this point, as will be understood from the above description, one side of a plate 130 has been immersed to a predetermined depth in a first dipping tank 150 and a second side has been similarly immersed in a second dipping tank 158. Further details of the dipping operation are explained below with reference to FIG. 14.

Figure 3:
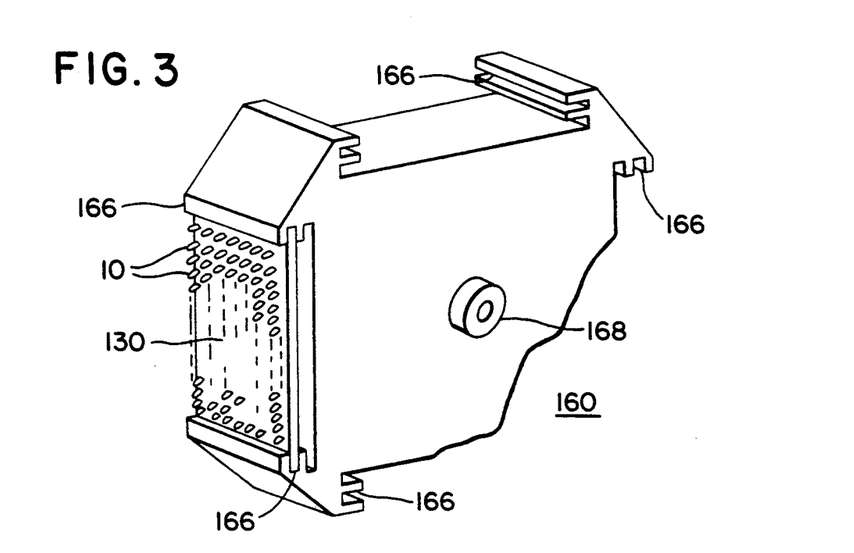
FIG. 3 is a partial perspective view of the apparatus of FIG. 2.

Incremental motion due to the plates urging against one another causes a plate 130 to enter the plate transfer means 160. This apparatus transports a plate 130 from a first location 162 to a second location 164. As will be understood by one of ordinary skill, there are a number of ways in which such a transfer is accomplished. For example, a rotating turret 160 having a number of means for receiving a plate may be aligned with the first and second locations 162,164 with the center of rotation of the turret located between them. Each incremental rotation of the turret would allow a new plate 130 to be received at the first location 162 and a plate 130 to be ejected at the second location 164. Thus, a turret having four sides would index in 90° increments. Such a device is illustrated in FIG. 3. Most preferably, a plate 130 is pushed into one of four sets of plate retainer means 166 which preferably grip the edges of the plate 130. The four plates and sets of retainer means are connected to a common hub 168, thereby permitting each plate to be indexed by rotation about the hub 168 until it has been moved from a first location 162 to a second location 164. Alternatively, a conveyor or the like could be used to deliver a plate 130 from a first location 162 to a second location 164. The conveyor is most preferably comprised of a conveyor belt and associated pulleys or a chain and sprocket arrangement. In either embodiment, the conveyor would also comprise means for retaining the plate.

Referring again to FIG. 2, although the second location 164 is illustrated as being disposed vertically above the first location 162, other embodiments of the present invention may require other spatial arrangements. Further, it is clear that the first and second locations 162,164 need not be physically separated if, for example, the apparatus of the present invention were a linear assembly line. However, the preferred embodiment illustrated permits full advantage to be taken of the numerous features disclosed herein and represents a compact, efficient utilization of manufacturing resources.

At the second location 164, a plate 130 is transferred to a conveyor means 170. The motive force to move the line of plates 130 along the conveyor means 170 is provided by each successive plate urging against the preceding plate, as occurred in the other portions of the apparatus. Therefore, the means provided at the second location for transferring the plate out of the transfer means 164 must be capable of creating sufficient force to push a plurality of plates, as illustrated. In certain embodiments of the present invention the housing 172 which surrounds the conveyor means 170 may also provide an area where means for washing and/or drying the plates may be located, such as shown at 171.

At the terminal end 176 of the conveyor means 170 a plate transport means 178 transfers plates from the conveyor means 170 to the dryer 180, explained below. In a preferred embodiment, the plate transport means 178 retains a pair of plates 130, aligns them with a receiving slot 182 and transfers them into the receiving slot 182. As illustrated, the plate transport means 178 preferably pivots downward to bring a pair of plates 130 into alignment with a slot 182. After the plates have been transferred into the slot, the transport means 178 pivots back to its original position and the dryer 180 incrementally rotates to bring an empty slot 182 into position, ready to receive another pair of plates.

Thus, a pair of plates 130 is loaded into the dryer 180, which cures the coatings 151,159. As illustrated, in a preferred embodiment the dryer 180 is of the rotating drum type. After each pair of plates is loaded, the dryer 180 progresses through about 330° of rotation. As the plates rotate they pass through streams of heated, conditioned air 184,186. Most preferably, energy efficiency is enhanced by collecting and recycling the heated air in collection ducts 186,188 after it has passed over and through the plates. As will be appreciated, the temperature, humidity, velocity of the air, as well as the rotational speed and number of slots in the dryer 180 are all dependent upon the curing characteristics of the coating materials 151,159 and the ambient environment. Also, numerous other dryer means may be used in the present invention to achieve the same result. For example, as shown in FIG. 4, the dryer 130 may be comprised of a series of conveyors, turrets, turntables, tracks or any of a number of means for passing a plurality of objects through a controlled environment for a predetermined time.

The plates 130 are then extracted from the dryer 180 by pulling on the plate 130 nearest the center of the dryer 180. The transfer out of the dryer 180 is preferably accomplished by extraction means 190 which engage a plate 130 and withdraws it from the dryer 180. The withdrawal of each plates also provides the force to move the preceding plates along the apparatus as explained above. However, in order to eject the coated products on a row-by-row basis, it is necessary to create a motion using the extraction means 190 which incrementally withdraws a plate, thereby incrementally advancing the plates which precede it. As each plate 130 is incrementally advanced, a row is aligned beneath means for ejecting the product 194. Further detail regarding the ejection means 194 is provided below. The ejected product is transported via a chute 196 to a hopper 200, where the finished product is collected and then transported in bulk for printing, inspection or other finishing operations. As explained with reference to other apparatus described above, the chute 196 and hopper 200 may be replaced by conveyors or other apparatus. Also, rather than being collected in bulk, the finished product may be ejected directly to the next operation, for example, into a means for printing a designation on the product.

Figure 4:
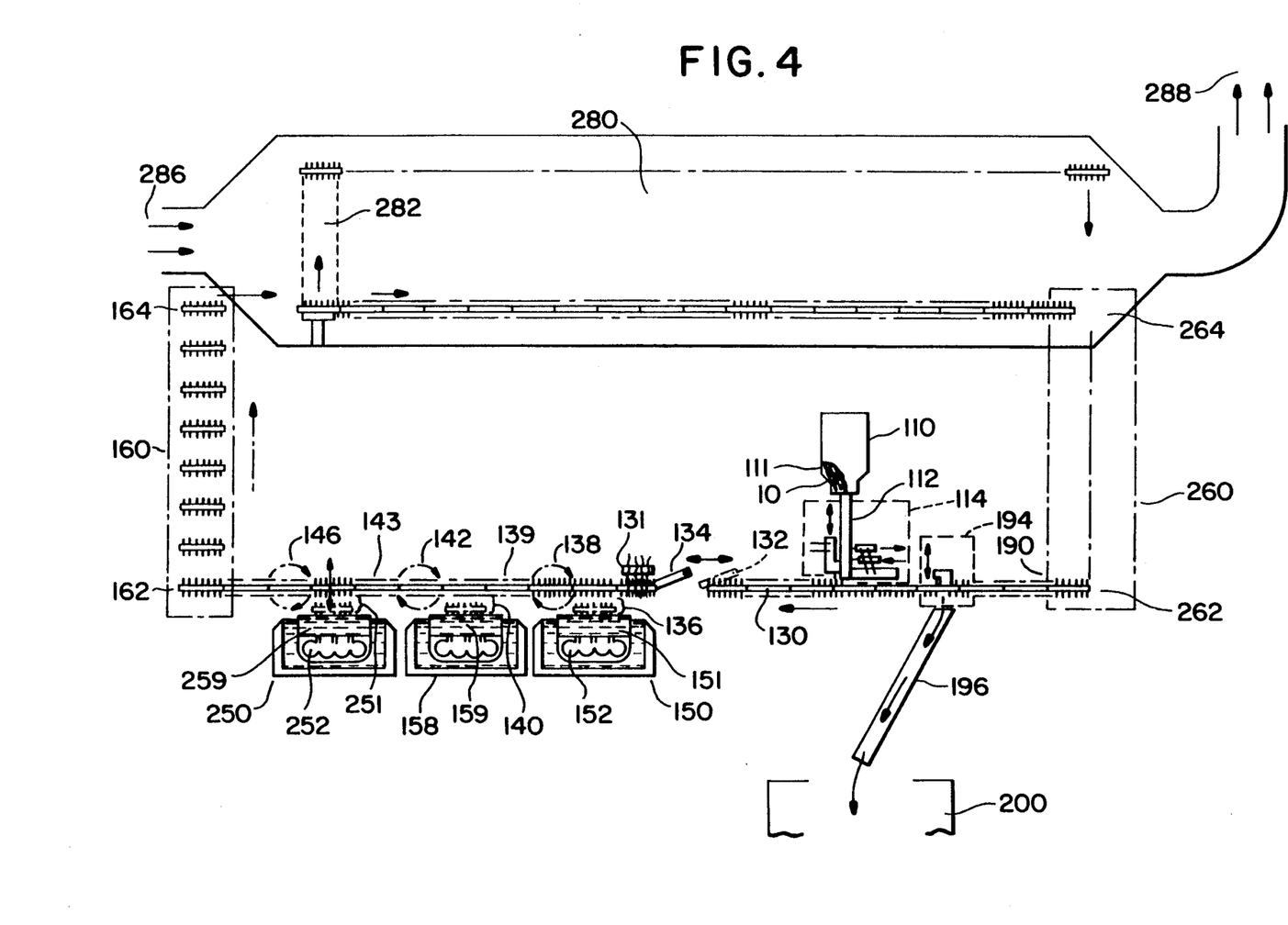
FIG. 4 is a partially schematic, partially diagrammatic illustration of another preferred embodiment of the apparatus of the present invention.

Another preferred embodiment of the apparatus of the present invention is shown in FIG. 4. In many aspects, the apparatus shown is similar to that described with reference to FIG. 2 and FIG. 3. The differences lie mainly in the number of dipping tanks and in the dryer design.

In the apparatus of FIG. 4, the feeding, loading and advancement of the plates 130 through a first and second dipping tanks 150,158 is similar to that shown in FIG. 2. However, a third dipping tank 250 has been added. As shown, each plate 130 is advanced to a third dwell location 143 and then to a third dipping means 251 for lowering and raising a plate. The third dipping tank 250 contains a third coating material 259 which is circulated by a pump 252, as in the other dipping tanks 150,158.

The plate 130 is next removed from the tank 250, incrementally advanced, and may again be rotated, as shown at 146. If the third rotation 146 is included, it may be desirable to omit or alter one of the first or second rotation sequences 138,142 described above. For example, a preferred coating sequence utilizing the apparatus of FIG. 4 would subcoat the product and apply a coating material to each end. Accordingly, the first dipping tank 150 would contain a subcoat and the first rotation 138 would be omitted. The second dipping tank 158 and third dipping tank 250 would contain a first and second coating material 159,259. The plate 130 would thus be rotated one and one-half revolution, as described above, at the locations shown at 142 and 146. One of ordinary skill will realize that other dipping sequences ar easily accomplished and that a fourth or more dipping tank could be added to the apparatus of the present invention.

After dipping has been completed, the plates are transferred in substantially the same manner as shown in FIG. 2 and FIG. 3. However, the upper conveyor is Preferably replaced with a "spiral" dryer 280. As shown in FIG. 4 the plates 130 are ejected at a second location 164 into a conveyor or other transport means 282 which retains and elevates the plates 130. By following the arrows, it can be seen that the plates travel in a vertical path and are also urged in horizontal increments. Although not shown, another vertical transport means 282 is provided at each increment. Thus, each plate takes an essentially spiral path through the space enclosed by the dryer 280. To ensure proper curing of the coating materials, conditioned air 286 is forced through the space and collected at an exit 288, to be recirculated, thus conserving energy.

After the plates 130 have traversed the length of the dryer apparatus 280, they are in an upper location 264 which is preferably similar to the second location 164 from which the plates 130 entered the dryer 280, but at the opposite end. A second rotating turret 260, similar to that described above in reference to FIG. 3, is preferably provided to transfer the plates from the upper location to the lower location 262. Of course, as set forth above, numerous other devices may be substituted in order to accomplish this function.

The remainder of the apparatus depicted in FIG. 4 is substantially similar to that described with reference to FIG. 2, and ejects and collects the finished product. As explained throughout the preceding paragraphs, the component apparatus and arrangement of the various portions of the overall apparatus of the present invention illustrated in FIGS. 2-4 represent preferred embodiments. Numerous other embodiments may be realized which perform the coating sequences described above. In the same manner, the following descriptions of preferred apparatus for performing operations described above are preferred embodiments for which any number of apparatus may be substituted by one of ordinary skill.

Figure 5:
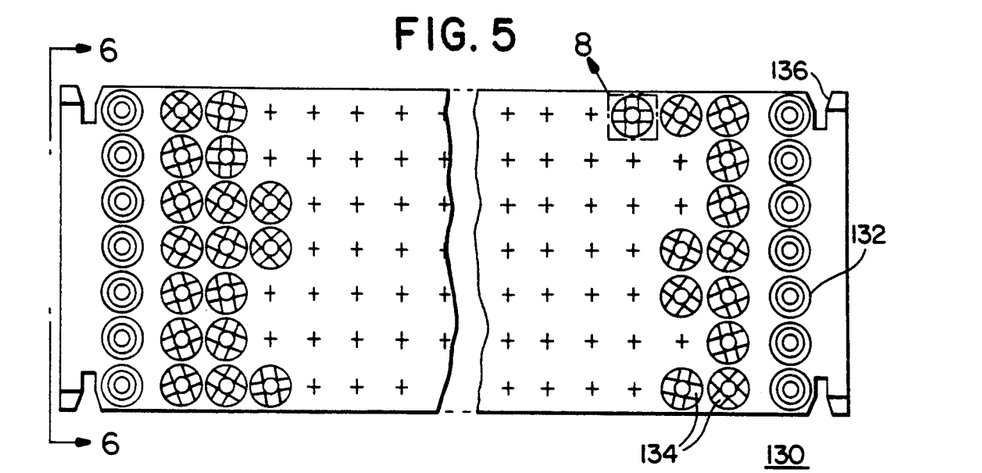
FIG. 5 is a top view of a plate made in accordance with certain aspects of the present invention.

As shown in FIG. 5, the present invention utilizes a novel double collet 134 and carrier plate 130 to constrain and transfer the product during the coating process. A number of collets 134 are disposed on a carrier plate assembly 130. The carrier plate 130 of the apparatus of the present invention is preferably constructed in a thickness sufficient to accommodate two caplets, or other specimens of the product to be coated in a manner aligning the product axially, wherein portions of each product to be dipped are exposed. As a further benefit of this construction, the distance through which each product is transferred during the dipping process is minimized. This feature reduces the time required to effect the transfer and also reduces the possibility of marring the coating during the process. The use of a carrier plate 130 thus enables the manufacturing process to be managed more effectively.

The individual plates 130 are easier to make, replace, clean and otherwise manage than a single continuous system. Plates bearing a few hundred collets 134 represent a preferred embodiment. In embodiments bearing smaller numbers of collets 134, the numerosity of the plates and associated fixturing equipment would unnecessarily increase costs. On the other hand, it is also not desirable to increase the number of products contained in each plate beyond a few hundred since the plates 130 would become unwieldy and difficult to manufacture within the preferred tolerance ranges necessary to ensure uniform product. The carrier plates 130 of the present invention are most preferably about 4-5 inches wide and contain 9 rows of collets 134, each row having 41 locations for retaining collets therein. In another preferred embodiment, 6 rows are used each having 30 locations, which thereby retains 180 collets 134.

Figure 6:
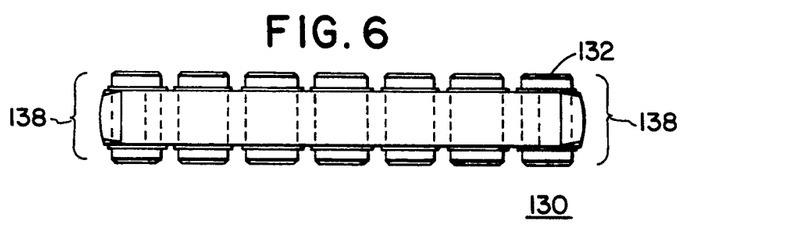
FIG. 6 is an end view of FIG. 5.

A preferred embodiment of the carrier plate 130 of the present invention is machined from tool plate aluminum. It is also preferred that the aluminum have a protective coating such as an adonized coating applied to its surface. The plate 130 is rectangular and symmetrical, having four evenly spaced slots 136 disposed near the four corners which engage holding and/or transport means. Also provided at either end are alignment and transport holes 132 which are used to manipulate the plate 130 as it is transferred from the dryer to the feeder described above. A plurality of collets 134, described below, are densely arrayed over the surface of the plate 130. As seen in FIG. 6, the plate 130 is preferably fabricated to have slightly curved longitudinal edges 138. This feature allows the rotations and other manipulations of the plates described to occur while reducing the occurrence of the corners of the plates coming into interfering contact with one another and chipping or deforming.

Figure 7:
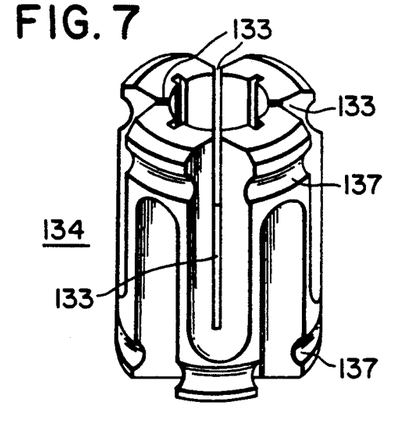
FIG. 7 depicts the double collet of the present invention in a perspective view.

An embodiment of the novel double collet 134 of the present invention is illustrated in FIG. 7. Most preferably, the collet 134 has a sequence of longitudinal slots 133 which create what is essentially a series of spring fingers which encircle the product (not illustrated). In the preferred embodiment shown in FIG. 7, the collet 134 is substantially cylindrical and four slots 133 are formed in each end. For clarity, reference numerals pointing out the slots opposite those designated as 133 are omitted. Also illustrated in FIG. 7 are grooves 137 disposed at either end of the collet which accept means for retaining the collet 134 in the plate 130, as explained below.

Figure 8:
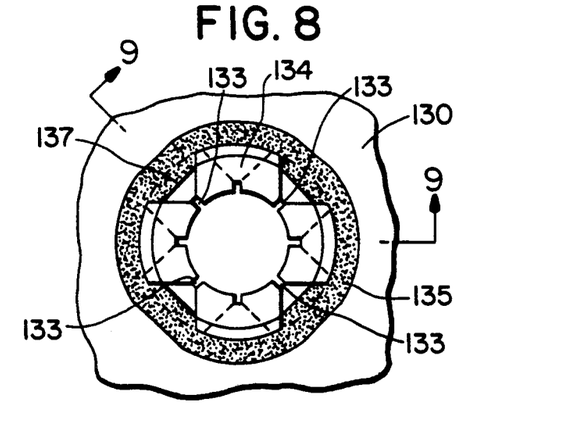
FIG. 8 is a top view of the collet of FIG. 7, shown mounted in the plate of FIG. 5 and taken along the lines shown in FIG. 5.
Figure 9:
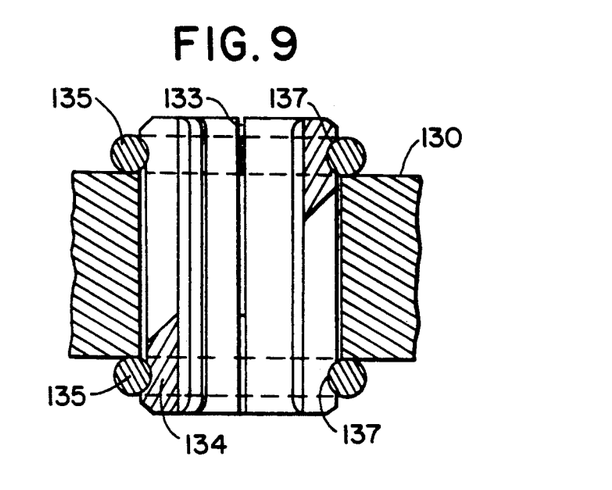
FIG. 9 is a sectional view taken along line 9—9 of FIG. 8 depicting the mounting and other details of the double collet of FIG. 7.

In FIG. 8, the installation of the collet 134 is illustrated. The collet 134 is shown inserted into the plate 130 and retained by an 0-ring 135 which is fitted around the circumference of a groove 137. As shown by the solid and dashed lines, a first set of slots 133 is offset from the second set, which permits a set of four spring fingers to be formed at either end of the collet 134. FIG. 9 illustrates a cross-section of the collet of FIG. 8, taken along line 9—9. In FIG. 9, it can be seen that the slots, such as those designated as 133, do not extend the full longitudinal length of the collet 134. It is also easily appreciated how the 0-rings 135 engage the grooves 137 and lock the collet 134 in place within the plate 130.

The collet 134 illustrated in FIGS. 5-7 may be modified or otherwise adapted depending upon the product 10 to be coated. It is generally preferred, however, that the collet 134 be of sufficient length to hold at least two of the product 10 to be coated, while leaving those portions to be coated exposed. As will be explained below, the collet serves to both retain the product 10 and, in certain embodiments, determine the portion which will be immersed in the coating.

Figure 10:
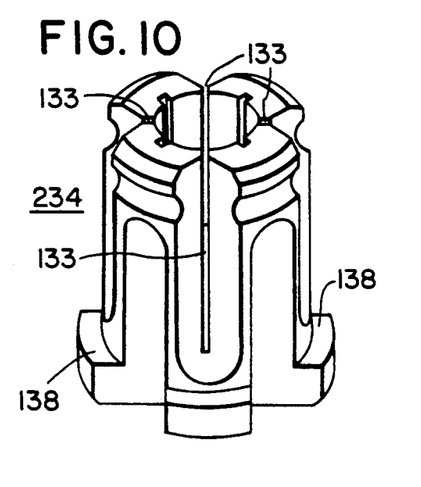
FIG. 10 is a perspective view of a preferred embodiment of the double collet of the present invention.
Figure 11:
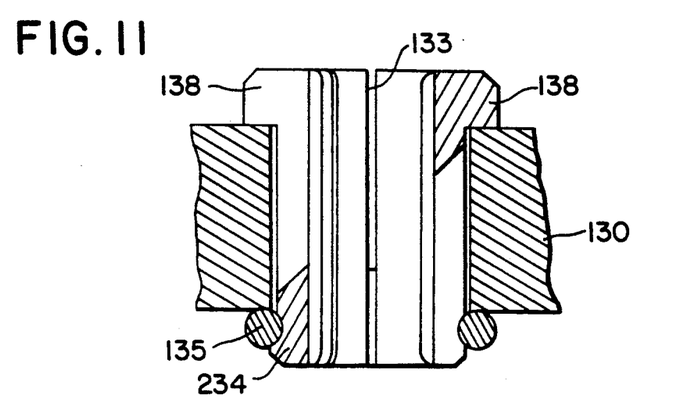
FIG. 11 is a sectional view similar to FIG. 9, taken along a line similar to that shown by line 9—9 in FIG. 8.

Another embodiment of a collet 234 for use in the plates 130 within the present invention is shown in FIG. 10. As illustrated, one of the grooves 137 has been replaced with a segmented annular shoulder 138 which performs substantially the same function as one of the 0-rings 135. As shown in FIG. 11, this embodiment of the collet 234 is placed in the plate 130 such that the extending portions of the shoulder 138 contact the surface of the plate 130 and prevents the collet 234 from sliding through the plate 130. As explained above and illustrated in FIGS. 7-9, an elastomeric member such as an 0-ring 135 is disposed in a groove 137 to retain the collet 234 in place. Thus, the embodiment of the collet eliminates the need for an O-ring 135 or similar component from at least one end of the collet 234.

Figure 12:
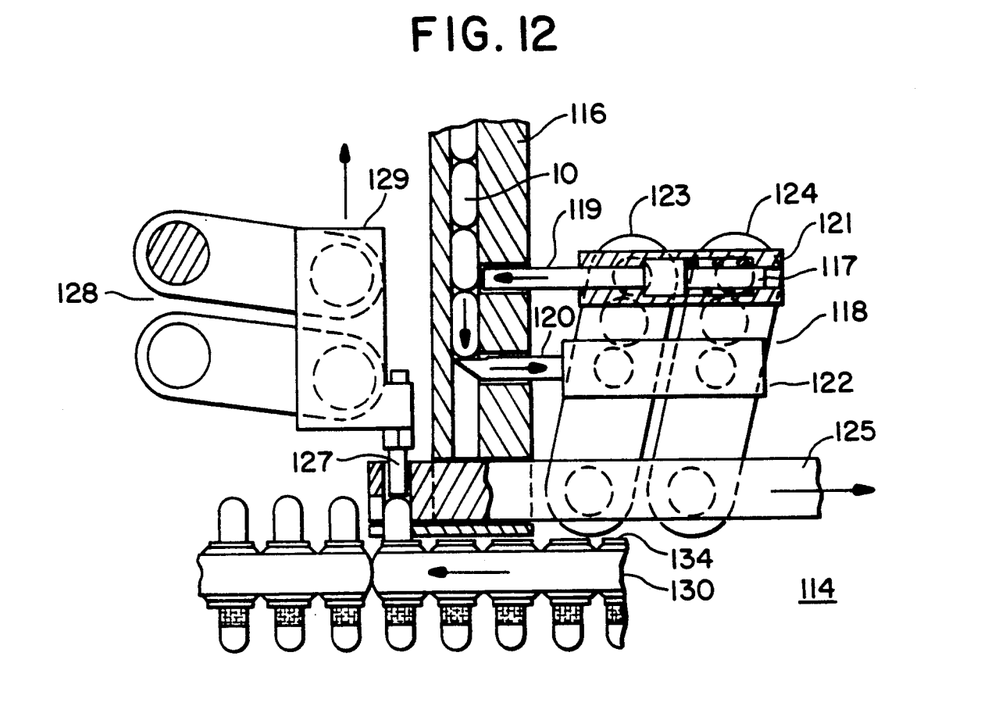
FIG. 12 is a partially broken away side view of the product insertion mechanism used in the preferred embodiment of FIG. 2.

Referring now to FIG. 12, a preferred embodiment of the feeder apparatus 114 is shown. The feeder apparatus 114 fills a plate 130 one row at a time. Most preferably, since the plate 130 holds a plurality of double collets 134, the feeder 114 fills one side of the plate 130. One of ordinary skill will understand that the when the process of the present invention is initiated using the preferred apparatus described, the plates 130 will be run with a single product 10 disposed within each double collet 134. In other words, the cycle will initially run "half-full" until the first plate 130 has reached the starting point, whereupon a second product will be introduced into each collet 134 and the "full" process will continue, ad infinitum, until the supply of product 10 is interrupted.

As shown in FIG. 12, a preferred embodiment of the product feeding apparatus 114 of the present invention comprises a feeder tube 116 which contains a linearly disposed plurality of product 10 to be inserted. It will be understood that FIG. 12 is a side view, partially cross-sectioned, therefore only one "column" of the product 10 is visible. However, in a preferred embodiment, a column of the product 10 is positioned over each collet 134 across an empty row of a plate 130.

During full cycle operation, at any point in time, a plate 130 will have open collets 134 on only one side. The other side will contain product which had been dipped with at least one of the two coatings. The open collets 134 are aligned with the feeding apparatus 114 by the indexed motion of the plate 130.

In a most preferred embodiment, the feeding apparatus comprises two sets of parallel linkages 118,128. The first set of linkages 118 causes product 10 to be fed in a single row and correctly positioned over a row of open collets 134. The second set of linkages 128 inserts the product into the collets to the correct depth. Thus, a column of product 10 is disposed within a feeder tube 116. Positioned to extend radially into and out of the feeder tube 116 are product control stops 119,120. Stop control bars 121,122 are attached to each product control stop 119,120. In turn, the control bars 121,122 are connected by parallel links 123,134. An alignment bar 125 is also connected to the links 123,124. In operation, the alignment bar 125 first moves in the direction shown by the arrow. This motion is transferred via the links 123,124 to the stop control bars 121,122. Since the lower stop bar 122 is disposed below the pivot points of the links 123,124 it moves in the same direction as the alignment bar 125 and is therefore withdrawn from a position where it is extending into the interior of the feeder tube 116. At the same time, the upper stop bar 121 is urged into the product 10. In order to permit the motion described, the upper stop bar 121 is provided with a spring mechanism 117 which permits the stop bar 121 to constantly urge against the product 10 while the lower stop bar 122 is withdrawn. As a result, the apparatus 114 is positioned as illustrated in FIG. 13.

It will thus be understood that when the alignment bar 125 is moved in the direction of the arrow in FIG. 12, the lower stop bar 122 is withdrawn and the upper stop bar 121 is resiliently urged against the product 10. Accordingly, in each feeder tube 116, a single product is allowed to fall down into the alignment bar 125 while the remainder of the product 10 in the tube 116 is held firmly in place, as illustrated in FIG. 13.

Figure 13:
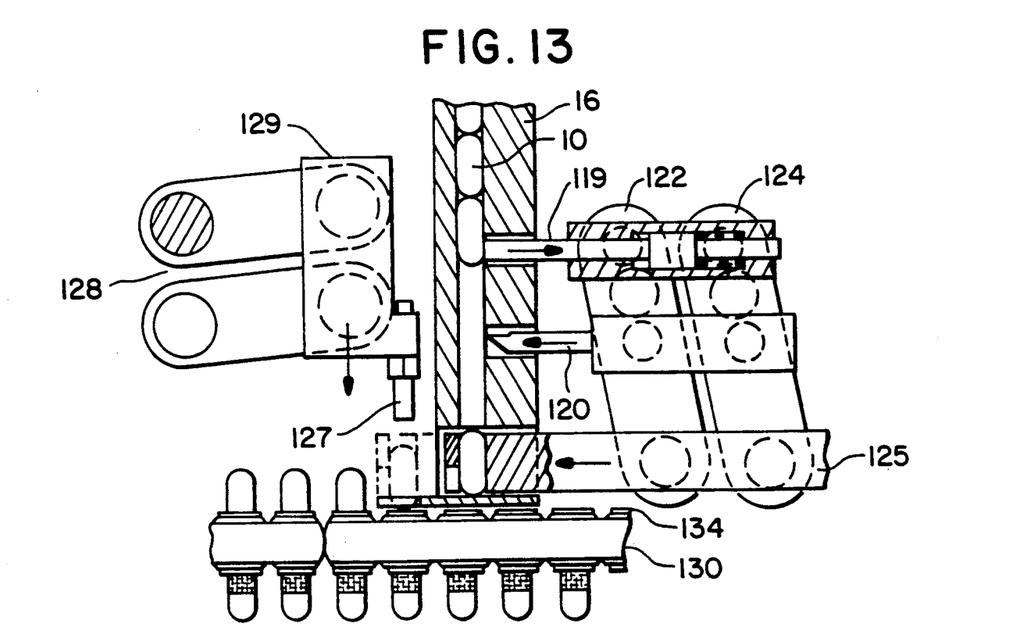
FIG. 13 is an alternate view of the apparatus of FIG. 12 showing the relative movement of the apparatus.

Once product has been dropped into the alignment bar 125, as shown in FIG. 13, the actual insertion into an open collet 134 will take place. As the alignment bar 125 moves in the direction shown by the arrow in FIG. 13, the product 10 to be inserted is moved to the open collet 134. At the same time, the upper stop bar 121 is withdrawn from the feeder tube 116 and the lower stop bar 122 extends inwardly, blocking the tube. Thus, the next row of individual product 10 is now disposed between the stop bars, as illustrated in FIG. 12.

Referring again to FIG. 13, as shown in phantom, aligning the row of product 10 with a row of open collets 134 also aligns the product with a row of pins 127, which are used to press the product into the open collets 134 to the desired height. The pressing is accomplished using a second parallel linkage mechanism 128 which drives a carrier 129 which has the pins 127 attached vertically downward, as shown by the arrow. The pins 127 are then immediately retracted, the plate 130 advances and the first set of linkages 118 repositions to feed a fresh row of product 10.

Figure 14:
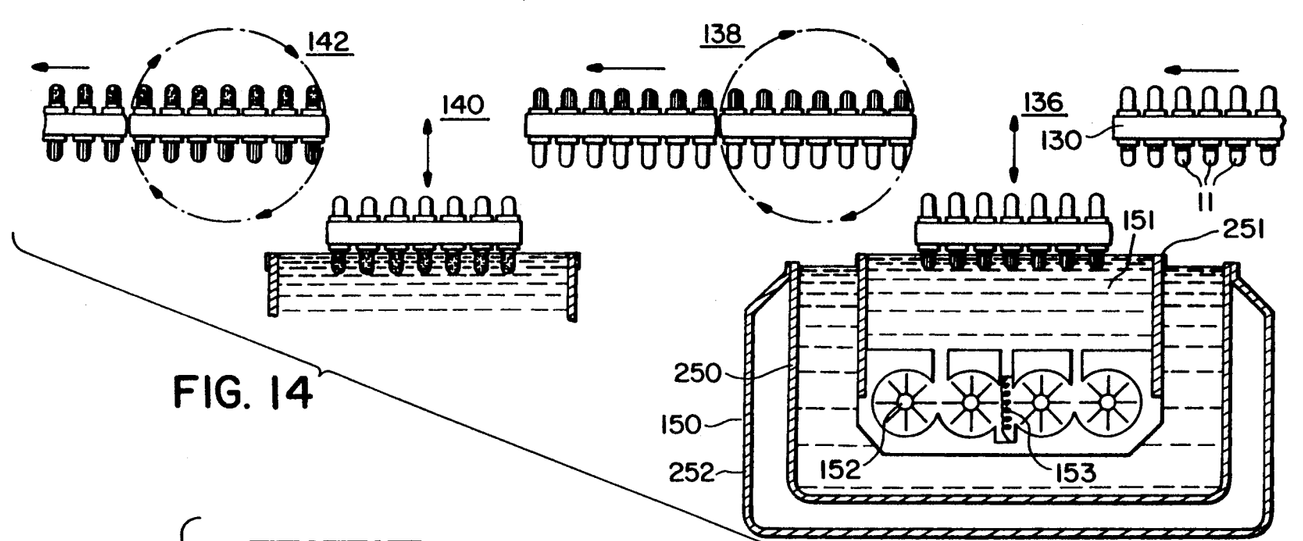
FIG. 14 is a partially sectioned and broken away view of the dipping apparatus of the present invention.

Turning now to FIG. 14 a partially sectioned and broken away view of the dipping apparatus of the present invention is shown. As explained above with reference to FIG. 2, during full cycle operation a plate 130 containing uncoated product 10 and partially coated product 11 is introduced by transfer means 134 to the dipping portion of the apparatus. It will be understood that the production sequence of the present invention, when running at full cycle, results in plate 130 in the condition illustrated. That is, uncoated product 10 is disposed in the upper section of the plate, while partially coated product is disposed in the lower section. Therefore, in a two-color process, the partially coated product 11 will have a first end already coated and the application of the second color will substantially complete the coating process if only one coat is being applied, allowing these products 11 to be ejected later in the cycle.

The plate 130 advances to the first dipping means 136, which lowers it into the first dipping tank 150. A cross-sectional view of a preferred embodiment of the first dipping tank 150 is shown. As illustrated, the tank 150 is comprised of two sections which contain a first coating material 151. The interior section 251 containing the material 151 actually applied to the products is in hydraulic communication with pump means 152. The pump means 152 draws additional coating material 151 from the reservoir formed by the outer section 250. The inner section 251 is disposed slightly above the upper edge of the outer section 250. The operation of the pump means 152 thus fills the inner section 251 to overfill, allowing excess coating material 151 to flow over the upper edge of the inner section 251. The excess coating material flows back into the outer section 250 and is recirculated. An outer cover 252 is also illustrated.

The preferred embodiment of the dipping tank 150 illustrated in FIG. 14 provides several important advantages. First, the provision of inner and outer reservoir sections 251,250 and pump means 152 allows the coating material 151 to be kept in constant circulation. This is a particularly important advantage where coatings such as gelatin are involved, since the material is not permitted to harden on the surface.

Additionally, the inner reservoir is kept out at a constant level. This advantage results in a highly consistent and accurate coating. If the transfer mechanism 136 can repeatedly lower a plate 130 to a given level within a certain tolerance, it is highly desirable for reasons of accuracy that the coating level in the inner section 251 remain at as constant a level as possible. In a most preferred embodiment, the pump means 152 is turned off momentarily, immediately before the plate 130 is lowered into the coating material 151. This permits any turbulence which has formed on the surface to dissipate, as well as any excessive meniscus which has formed due to overfilling. As will be understood by one of ordinary skill, a meniscus will always be present, but will most pronounced near the edges of the inner section 251, a portion into which product is most preferably not dipped. Therefore, the surface of the coating material 151 within the inner section 251 is substantially level across that portion of the surface where the product is dipped.

In addition to pump means 152, heating and water metering apparatus 153 can be provided to maintain the desired viscosity and temperature of the coating materials. Such heating and water metering apparatus may be integral with the pump means 152, as shown, or disposed in their vicinity. Alternatively, one of ordinary skill can see how any of the numerous variations of heating coils and the like can be introduced into either of the inner section 251, the outer section 250 or the space between the outer cover 252 and the outer section 250. The water metering portion of the apparatus preferably provides deionized water to the gelatin or other water soluble coating in order to regulate its viscosity.

As explained above with reference to FIG. 2, after the plate is removed from the first dipping tank 150, it is indexed, rotated one and one-half revolutions, and indexed again until it is disposed over the second dipping tank 158. At this point, the uncoated product 10 is positioned to be immersed in the second coating material 159 contained in the second dipping tank 158. Most preferably, the second dipping tank 158 is substantially the same as the first dipping tank 150. The plate 130 is then removed and rotated one and one-half revolutions. The plate 130 and the product 10 contained therein has now been returned to its initial orientation. It will be understood that at this Point the plate 130 contains a plurality of product in its lower section which has been dipped in both dipping tanks 150,158. The upper section of the plate contains a similar number of product which have been dipped only in the second dipping tank 158. The uncoated end of this latter product remains within the collets 134 disposed within the plate 130. The plate 130 is then indexed to a further processing position.

Although the dipping apparatus and sequence of the present invention has been set forth with reference to specific embodiments, one of ordinary skill will immediately realize that modifications or additions can be easily made to the methods and apparatus disclosed without departing from this general principle. As explained above with reference to FIG. 4, other dipping tanks may be added to provide precoating or further coatings in additional colors or a clear, protective coating may be added. Also, intermittent stations may be inserted between the stages of the apparatus shown. For example, heating apparatus or spraying apparatus may be added before or after either the dipping means or the rotating means. Finally, certain aspects of the present invention, such as the sequence of dipping and rotating the plates, may be practiced in conjunction with other apparatus beyond the specific apparatus disclosed.

Figure 15:
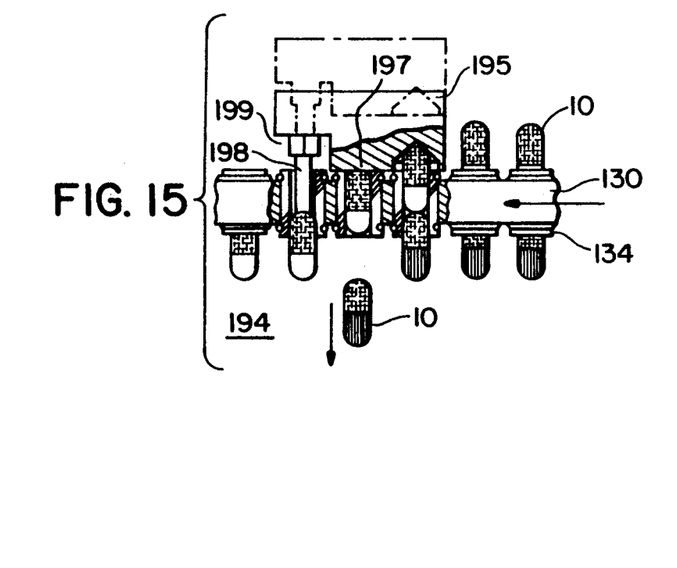
FIG. 15 is a partially broken away side view of the product ejection mechanism used in the apparatus of the present invention.

Illustrated by FIG. 15 is a preferred embodiment of the ejection means 194 of the present invention. As described above, after the plates 130 are removed from the drying oven 180, or other final operation, it is desirable to eject that product 10 which has been through the full cycle of the apparatus and thus, insofar as the coating is concerned, represents a "finished" product. The ejection means of the present invention provides an improvement over that disclosed by U.S. Pat. No. 4,820,524. As shown therein, the ejection process forced the coated product through the full length of a collet, thereby presenting the possibility of scraping some of the coating from the product, particularly in the area comprised of a double thickness of coating material which simulates a capsule-like appearance. The ejection apparatus explained below substantially eliminates this possibility.

In a preferred embodiment, the ejection means 194 comprises apparatus which ejects the finished product 10 from the plate 130 in a controlled manner. As illustrated, a plate 130 retains two specimens of the product 10 in each collet 134. The broken away portion of FIG. 15 illustrates that a fully coated and finished product 10 is disposed in an axially aligned manner beneath a second specimen of the product while within a collet 134. Thus, in a preferred embodiment, the ejection means 194 ejects the finished product 10 and positions the second product in an orientation to receive further coating. In certain embodiments the second specimen of product 10 will take the position of the specimen which has been ejected. However, after ejecting the finished product, the collet 134 will be ready to accept a fresh, uncoated specimen from the feeder apparatus 114, explained above.

As illustrated in FIG. 15, a preferred embodiment of the ejector means 194 moves between a first position and a second position, shown in phantom. An initial positioning means 195 is provided to orient the product 10 and begin the process of ejection. Most preferably, a substantially cone-shaped portion contacts the product. The product is thus aligned with the apex of the cone and moved through the collet 134 until the ejection means 194 comes into contact with the plate 130. It should be noted that the axially aligned product specimens of product 110 are urged together such that the motion of one is transferred to the other.

After initial orientation, the ejection apparatus 194 is withdrawn to the position shown in phantom and the plate is indexed in the direction of the arrow shown in FIG. 15. The indexing brings the product in the upper portion of the plate 130 beneath the ejection means 197. Most preferably, the ejection means 197 is merely a flat plate or flat portion which is disposed a predetermined height above the plate 130. As the ejection apparatus 194 is again brought into contact with the plate 130, the product in contact with the ejection means 197 is driven further into the collet 134 until it is approximately flush therewith, as shown. This motion causes the finished product 10 to be driven beyond the retaining means of the collet 134 and thereby be ejected. Thus, the present invention uses an ejector unlike that disclosed in U.S. Pat. No. 4,820,524, since the second color applied to the product is not pushed through the length of the collet 134.

The ejection apparatus 194 is next again withdrawn to the position shown in phantom. The plate 130 advances to position the row of collets 134 from which the finished product has been ejected beneath the product positioning means 198. In a most preferred embodiment, the positioning means 198 comprises a pin having means for adjusting the length of the pin 199 relative to the ejection apparatus 194. As illustrated by FIG. 15, the adjustment of the pin 198 is accomplished by the pin 198 being threaded into a stop nut 199. In a most preferred embodiment, the pin 198 will be concave at its distal end to enhance contact and alignment with the product being positioned.

In operation, the pin 198 is brought into contact with and urged against the product which remains in the collet 134 by the downward motion of the ejector apparatus 194. When the ejector apparatus has reached the lower limit of its travel, the product will have been urged through the collet, and at least the portion to be further coated will be exposed. The amount of this exposure is defined by the length of the pin 198. In other embodiments, stops, cams or other well know devices can replace the adjustable pin 198 and provide adjustable motion to the ejector apparatus 194 itself or a portion thereof.

Thus, as set forth immediately above, the ejector apparatus 194 initially positions the product 10 which is aligned above the product 10 to be ejected, urges the product through the collet 134 until the finished product 10 is ejected and finally urges the non-ejected product into substantially the same position as the product which was ejected. As illustrated, the process by which the present invention most preferably ejects the finished product 10 is related to the indexing of the plates 130 which forms a part of the overall operation of the apparatus. In other embodiments, such indexing may not exist and therefore the ejector apparatus 194 will itself be indexed or placed on a turret or otherwise adjusted to provide the ejection function. Also, the apparatus shown in FIG. 15 can be modified to align and eject the product in a single stroke, rather than in the three increments described. Finally, the ejector may be adjusted to fully eject a single product from the plates in order to empty or "run out" the plates at the end of a cycle.

The present invention also provides methods of coating a medicament. Initially, means for retaining product must be provided. In order to begin full cycle operation, in a preferred method, the means for retaining product will already have a first specimen of the product disposed therein. A portion of the first specimen will protrude downwardly or otherwise beyond the surface of the means for retaining product, thereby defining a first end. Since the preferred method described herein will take place only after the initial "half-full" run has been completed, another portion of the first specimen will already have a coating.

Thus, in full operation, a second specimen of the product to be coated is then provided. This second specimen is inserted into the means for retaining product, such that a portion of the second specimen protrudes, thereby defining a second end. The second end of the product is then lowered into means for creating a coating. Most preferably, this step comprises lowering the means for retaining product into the coating. The means for retaining product is the rotated to cause said second end to be downwardly protruding and the second end is then lowered into a second means for creating a coating. After this step, the means for retaining product is again rotated thereby causing the first end to be again downwardly protruding. If only two coatings are being applied, as in the preferred embodiment, the coating is then cured. Most preferably, this is accomplished by heating and circulating conditioned air through the product. After the coating has cured, the second end is depressed until an uncoated portion of said second specimen protrudes in a manner similar to said first specimen prior to the initiation of the coating cycle. Thus, the first specimen is fully coated and released from the means for retaining product. The said second specimen, however, remains held by said means for retaining a product substantially in the same position as the first specimen, and the cycle may be repeated.

Although certain embodiments of the present invention have been described in detail, it is not intended that the invention be so limited. Accordingly, reference should be had to the appended claims to determine the full scope of the present invention.

What is claimed is:

1. Carrier apparatus for processing a plurality of a product, comprising a plurality of collet means for maintaining a product in a fixed orientation wherein at least two specimens of the product are retained within at least one of the collet means and including means for retaining the collets comprising a circumferential depression near at least a first end of the collet; and the means for retaining the collets comprises at least one resilient member disposed in said circumferential depression.

2. The apparatus of claim 1, wherein the carrier apparatus is a plate means having two major surfaces.

3. The apparatus of claim 1, wherein the plate means is comprised of aluminum.

4. The apparatus of claim 3, wherein the plate means is further comprised of a protective coating.

5. The apparatus of claim 1, wherein the protective coating comprises an adonized surface.

6. The apparatus of claim 1, wherein the collet means comprises a substantially cylindrical portion, having a substantially cylindrical bore therethrough, the collet means of sufficient length to retain at least two specimens of the product.

7. The apparatus of claim 1, wherein the collet means comprises one or more resilient members which urge against the product.

8. The apparatus of claim 7, wherein the collet means further comprises longitudinal slots defining said resilient members.

9. The apparatus of claim 1 further comprising means for retaining the collets.

10. The apparatus of claim 1, wherein the resilient member is comprised of an elastomeric O-ring.

* * * * *